United States Patent
Sternby et al.

(10) Patent No.: US 10,420,797 B2
(45) Date of Patent: Sep. 24, 2019

(54) ANTICOAGULATION FLUID COMPRISING CITRATE AND PHOSPHATE

(71) Applicant: Gambro Lundia AB, Lund (SE)

(72) Inventors: Jan Sternby, Lund (SE); Anders Wieslander, Lund (SE)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 14/780,359

(22) PCT Filed: Apr. 30, 2014

(86) PCT No.: PCT/EP2014/058912
§ 371 (c)(1),
(2) Date: Sep. 25, 2015

(87) PCT Pub. No.: WO2014/177656
PCT Pub. Date: Nov. 6, 2014

(65) Prior Publication Data
US 2016/0038540 A1 Feb. 11, 2016

(30) Foreign Application Priority Data

Apr. 30, 2013 (SE) ...................................... 1350533
Apr. 30, 2013 (SE) ...................................... 1350534

(51) Int. Cl.
| | | |
|---|---|---|
| *A61K 33/42* | (2006.01) | |
| *A61K 33/00* | (2006.01) | |
| *A61K 9/08* | (2006.01) | |
| *A61K 31/7004* | (2006.01) | |
| *A61K 31/194* | (2006.01) | |
| *A61K 33/06* | (2006.01) | |
| *A61K 33/10* | (2006.01) | |
| *A61K 33/14* | (2006.01) | |
| *A61K 9/00* | (2006.01) | |
| *A61M 1/16* | (2006.01) | |

(52) U.S. Cl.
CPC ............ *A61K 33/42* (2013.01); *A61K 9/0019* (2013.01); *A61K 9/08* (2013.01); *A61K 31/194* (2013.01); *A61K 31/7004* (2013.01); *A61K 33/00* (2013.01); *A61K 33/06* (2013.01); *A61K 33/10* (2013.01); *A61K 33/14* (2013.01); *A61M 1/1654* (2013.01)

(58) Field of Classification Search
CPC ..................................................... A61K 33/42
See application file for complete search history.

(56) References Cited

U.S. PATENT DOCUMENTS

| 5,635,026 A | 6/1997 | Kettunen et al. |
| 6,743,191 B1 * | 6/2004 | Chang .................... A61K 33/42 |
| | | 210/646 |
| 2007/0062861 A1 | 3/2007 | Lannoy |
| 2007/0110829 A1 | 5/2007 | Tolwani et al. |
| 2008/0015487 A1 | 1/2008 | Szamosfalvi et al. |
| 2009/0221948 A1 * | 9/2009 | Szamosfalvi ....... A61M 1/3672 |
| | | 604/6.07 |
| 2012/0022423 A1 * | 1/2012 | Sternby ................ A61K 31/191 |
| | | 604/6.07 |

FOREIGN PATENT DOCUMENTS

| JP | 02-152923 | 6/1990 |
| JP | 2001-178815 | 7/2001 |
| JP | 2009-527343 | 7/2009 |
| WO | 2007/101064 A2 | 9/2007 |
| WO | 2007101064 | 9/2007 |
| WO | 2010/112538 A1 | 10/2010 |
| WO | 2011/109356 A2 | 9/2011 |

OTHER PUBLICATIONS

Tolwani et al. A Practical Citrate Anticoagulation Continous Venovenous Hemodiafiltration Protocol for Metabolic Control and High Solute Clearance. Jan. 2006.*
Ashton et al., "Recent Advances in Continuous Renal Replacement Therapy: Citrate Anticoagulated Continuous Arteriovenous Hemodialysis," ANNA Journal, Jun. 1991, vol. 18, No. 3, pp. 263-267 and 329.
Broman et al., "Phosphate-containing dialysis solution prevents hypophosphatemia during continuous renal replacement therapy," Acta Anaesthesiol Scand 2011; 55: 39-45.

* cited by examiner

*Primary Examiner* — Adam C Milligan
*Assistant Examiner* — Sarah Alawadi
(74) *Attorney, Agent, or Firm* — K & L Gates LLP

(57) ABSTRACT

The present invention concerns an anticoagulation fluid comprising 10-40 mM citrate and 0.1-4 mM phosphate. The anticoagulation fluid is to be used for regional citrate anticoagulation in an extracorporeal blood circuit. The anticoagulation fluid may be combined with at least one treatment fluid in the dialysis treatment, and it may be included in a system for regional citrate anticoagulation in an extracorporeal blood circuit.

8 Claims, 4 Drawing Sheets

US 10,420,797 B2

ANTICOAGULATION FLUID COMPRISING CITRATE AND PHOSPHATE

PRIORITY CLAIM

This application is a 371 National Stage Application of International Application No. PCT/EP2014/058912, filed Apr. 30, 2014, which claims priority to and the benefit of Swedish Application No. 1350533-4, filed Apr. 30, 2013, and claims priority to and the benefit of Swedish Application No. 1350534-2, filed Apr. 30, 2013, the disclosures of each of which are incorporated by reference herein in their entireties.

TECHNICAL FIELD

The present invention concerns an anticoagulation fluid for dialysis therapy. More particularly it relates to a citrate anticoagulation fluid which also comprises phosphate. The anticoagulation fluid is to be used for regional anticoagulation in an extracorporeal blood treatment.

BACKGROUND

Dialysis is the indicated treatment for patients with renal insufficiency. The removal of waste substances and excess of fluid from the blood is effected by transfer to an external fluid or by replacement of plasma liquid with an external fluid. Various dialysis techniques with associated dialysis fluids may be differentiated. Which dialysis technique to use, depends on the type of patient.

In the case of patients suffering from chronic renal insufficiency, the patient receives dialysis therapy 3-5 hours, about three times per week. The dialysis therapy is usually performed at a dialysis center, although home dialysis is also possible. When home dialysis is performed the patient is free to perform dialysis more frequently and also in a more gentle treatment with longer duration, i.e. 4-8 hours per treatment and 5-7 treatments per week. The dose and treatment duration may be adjusted to each patient's demands and needs.

In the case of patients suffering from acute renal insufficiency, a continuous treatment throughout the entire day, and in some cases for several weeks, a continuous renal replacement therapy (CRRT), is the indicated treatment.

Continuous renal replacement therapy (CRRT) can also be used in treatment of chronic renal insufficiency by using a wearable artificial kidney system. Such a system is for example disclosed in US 2008/058696.

In a dialysis treatment a portion of the patient's blood stream is lead into an extracorporeal blood circuit comprising a semipermeable membrane in which the removal of waste substances is performed and then the cleansed blood is lead back to the patient. The semipermeable membrane has a blood side and a dialysate side.

When the removal of waste substances is effected by transfer to an external fluid, the waste substances and excess fluid are transferred by diffusion through the semipermeable membrane wall into a dialysis fluid flowing on the dialysate side of the semipermeable membrane. Simultaneously as the waste substances are transferred from the blood, through the semipermeable membrane wall and into the dialysis fluid, solutes and nutrients may diffuse in the opposite direction from the dialysis fluid, through the semipermeable membrane and into the blood. This technique is called hemodialysis.

When the removal of waste substances is made by replacement of plasma liquid with an external fluid, a portion of the plasma liquid is removed from the blood by means of convective flow through the semipermeable membrane, and an external fluid (also called an infusion fluid, a replacement fluid or a substitution fluid) is added to the blood stream. This technique is called hemofiltration.

Finally the removal of waste substances may also be made by a combination of hemodialysis and hemofiltration, thus the removal of waste substances is provided by a combination of diffusion and convection through the semipermeable membrane, and the solutes and nutrients are added both by infusion in the blood stream and by diffusion from the dialysis fluid through the semipermeable membrane and into the blood. This technique is called hemodiafiltration.

Common for all the above disclosed techniques is that the blood is withdrawn from the patient continuously into an extracorporeal blood circuit, in which the removal takes place, and the "cleansed" blood is returned to the patient. When blood is removed from its normal environment within the blood vessels, the blood coagulation cascade is initiated, and in order not to clog the extracorporeal blood circuit with the coagulating blood, means for anticoagulation have to be provided.

The fluids used during the dialysis treatment, thus the dialysis fluid, the infusion fluid (also named replacement fluid or substitution fluid), have been given the comprehensive term "treatment fluids" in the following.

The treatment fluids used in all the above dialysis techniques contain mainly electrolytes like sodium, magnesium, calcium, potassium, an acid/base buffer system and optionally glucose or a glucose-like compound. All the components in the treatment fluids are selected to control the levels of electrolytes and the acid-base equilibrium within the blood.

The treatment fluids are today often prepared from different types of concentrates. It may be liquid concentrates of different degree of concentration, where the acid/electrolyte part is separated from the buffer part before use.

The treatment fluids may be prepared from concentrated volumes of 0.5-8 L in bags for bedside use, or prepared from volumes of 5-20 L in canisters, which still are for bedside use. The treatment fluids may also be prepared from concentrates in central tanks in volumes of 300-1000 L.

The concentrates may also be provided as dry powder concentrate, to be dissolved and diluted into the determined concentrations.

When using bicarbonate as a buffer component in the treatment fluids, bicarbonate may also be provided as a dry concentrate for on-line-preparation of saturated bicarbonate containing concentrate. The saturated bicarbonate containing concentrate is thereafter mixed with an acid/electrolyte concentrate and further diluted with purified water to produce the on-line prepared treatment fluid.

The treatment fluids may also be provided in bags. In some cases the treatment fluids are provided in multi-compartment bags, in which the acid/electrolyte part is contained within one compartment, and the buffer part is contained in another compartment, and where the two parts are mixed right before use in a way to maintain sterility of the treatment fluid to provide a ready-for-use treatment fluid. Also, the treatment fluid may be provided in single compartment bags.

Patients in need of dialysis are often hyperphosphatemic when starting the dialysis treatment. However, during the dialysis treatment phosphate is removed from the patient and if no counteraction is taken the patients may become hypophosphatemic. In order to counteract this loss of phosphate during the treatment, phosphate containing dialysis fluids have been developed and introduced on the market. As a consequence the variability of patient serum phosphate levels as well as the incidences of hypophosphatemia has been significantly reduced.

Anticoagulation for dialysis patients are today often provided by heparin injections or by regional anticoagulation using citrate infusion into the extracorporeal blood.

Citrate containing fluids are previously known. A citrate containing replacement fluid is described in WO 2007/059145 A2.

In US2008/0015487A1 is a replacement fluid comprising citrate and phosphate described. However, due to the low content of citrate this fluid is considered unsuitable as anticoagulation fluid.

The use of citrate as an anticoagulant for dialysis patients is increasing. A fluid containing sodium citrate and/or citric acid is then infused close to the blood access where the blood exits the patient and enters into the extracorporeal blood circuit. Citrate acts as an anticoagulant by lowering the ionized calcium concentration within the plasma, through calcium citrate complex formation. Ionized calcium is essential for the blood coagulation cascade. If the ionized calcium level is lowered well below 0.5 mM, the blood coagulation cascade is prevented. Citrate that exists in the blood is rapidly metabolized, and theoretically three bicarbonate ions are formed from each citrate ion. As the citrate concentration is lowered in the metabolism, citrate complex bound calcium is released and returns to ionized calcium.

Today citrate is delivered to the clinics in sterilized pre-prepared anticoagulation fluid bags with citrate concentrations between 10-400 mM. Depending on the citrate concentration of the pre-prepared anticoagulation fluid, many liters of this citrate may be infused into the patient in order to provide proper anticoagulation during the treatment.

However, the use of many liters of the pre-prepared anticoagulation fluid often leads to situations when too much of the desired treatment dose is supplied by the anticoagulation fluid leaving too little room for using other treatment fluids, such as dialysis fluid and/or added infusion fluid (also named replacement fluid or substitution fluid). Thus, this limits the possibility of balancing the correct amount of phosphate within the blood in order to compensate the phosphate removal in the semipermeable membrane. One way of rendering this problem is to include the phosphate in the anticoagulation fluid.

SUMMARY OF THE INVENTION

One object of the present invention is to provide an anticoagulation fluid for regional citrate anticoagulation in an extracorporeal blood circuit. The anticoagulation fluid comprises citrate in combination with phosphate.
The anticoagulation fluid of the invention provides a possibility to balance the amount of phosphate within the blood throughout a dialysis treatment.

In one embodiment of the invention is an anticoagulation fluid for regional citrate anticoagulation in an extracorporeal blood circuit provided, wherein the anticoagulation fluid comprises 10-40 mM basic citrate; 0-5 mM acid citrate; and 0.1-4 mM phosphate. Typically, the anticoagulation fluid may comprises citrate in an amount of 15-40 mM basic citrate; preferably 18-40 mM basic citrate; and more preferably 20-40 mM basic citrate.

In another embodiment of the invention the anticoagulation fluid comprises 0.1-3 mM phosphate. More particularly, the anticoagulation fluid comprises 0.5-2.0 mM phosphate, preferably 0.8-2 mM phosphate.

Further, an embodiment of the invention is an anticoagulation fluid comprising citrate and phosphate in concentrations as above, and in addition also comprises 0-150 mM sodium ($Na^+$). The anticoagulation fluid may comprise the sodium in a physiological amount, such as between 130-150 mM sodium.

In one embodiment of the invention, the anticoagulation fluid of the invention has a pH between 6 and 8, preferably pH between 6.5 and 8. More preferably, the pH of the anticoagulation fluid is between 7 and 8, such as 7.4, the physiological pH.

A further embodiment of the invention is an anticoagulation fluid comprising, in addition to the basic citrate and the phosphate, 0-1.5 mM magnesium, 0-4 mM calcium, 0-5.0 mM potassium, 0-11 mM glucose, and 0-150 mM sodium, such as 130-150 mM sodium.

An anticoagulation fluid as defined herein comprises 10-40 mM basic citrate; 0-5 acid citrate; 0.1-4 mM phosphate; 0-1.5 mM magnesium, 0-4 mM calcium, 0-5.0 mM potassium, 0-11 mM glucose, and 0-150 mM sodium. The present invention concerns an anticoagulation fluid to be used as part of a multipart fluid system for dialysis therapy, wherein the multipart fluid system comprises an anticoagulation fluid and at least one treatment fluid from the group consisting of dialysis fluid and infusion fluids. With the anticoagulation fluid according to the present invention it has surprisingly been shown that a separate phosphate infusion may be avoided, and that the phosphate level is balanced throughout the dialysis therapy.

Even though phosphate can be added also to treatment fluids there are several advantages to have phosphate in the anticoagulation fluid. A fairly large part of the treatment dose is often delivered via the anticoagulation fluid. The impact by variations in the treatment fluid flow rates on the phosphate level in the blood returned to the patient will therefore be rather small. It is thus possible to vary the treatment dose by varying the treatment flow rates without affecting the phosphate balance too much.

Another advantage is that the anticoagulation fluids are often much less complex than the treatment fluids, with much fewer components included. The total number of different products will therefore be much less if phosphate is included in the anticoagulation fluid, since it is necessary to provide products with a number of different concentrations or each component. As an example, we may have one anticoagulation fluid that can be used with a number of different treatment fluids, that include 2 levels each of magnesium and glucose, and 3 levels each of potassium and calcium. The total number of products would then be 2*2*3*3=36 different treatment fluids and 1 anticoagulation fluid. If we add 2 levels of phosphate to the treatment fluids this would create 36 more products, but if we add 2 levels of phosphate to the anticoagulation fluid, only 1 more product is created.

Yet another advantage is that the flow rate of anticoagulation fluid is usually automatically adapted to the blood flow rate in order to achieve the same level of anticoagulation irrespectively of the blood flow rate. The same will happen to phosphate if phosphate is added to the anticoagulation fluid, i.e. the concentration of phosphate in the blood after infusion of the anticoagulation fluid will be the same regardless of the blood flow rate.

Depending on the total treatment regime for a patient, including the prescription of dialysis as well as nutritional fluids, the demand for phosphate supplementation may vary. If the phosphate is delivered in the anticoagulation fluid we can vary the amount of phosphate delivered to the patient by varying the blood flow rate. This will only marginally vary the treatment dose, since, in CRRT, the delivered dose of treatment is mainly determined by the flow rates of the treatment fluids. This is yet another advantage with the current invention compared to having phosphate in the treatment fluids.

It is well known that higher citrate levels in the anticoagulation fluid lead to lower flow rates of this fluid in order to achieve the same level of anticoagulation. In order to get the same level of phosphate in the blood when using different anticoagulation fluids it is therefore natural to let the phosphate level vary together with the citrate level, so that fluids with higher citrate level also have higher phosphate levels.

Depending on whether the treatment fluids used together with the anticoagulation fluid contain phosphate or not, the phosphate concentration in the anticoagulation fluid may preferably be different. If the treatment fluids contain phosphate the concentration of phosphate in the anticoagulation fluid could be close to physiological, i.e. 0.6-1.2 mmol/L, whereas the higher ranges of phosphate in the anticoagulation fluid, 1.2-4 mmol/L could be used if the treatment fluids do not contain any phosphate.

With the anticoagulation fluid of the present invention it is also possible to limit the volume of anticoagulation fluid needed to achieve a certain level of anticoagulation by increasing the concentration of citrate. It is thus desirable to increase the concentration of citrate beyond 10 mM, preferably above 15, 18, 20, or 25 mM.

DEFINITIONS

Figure 1:
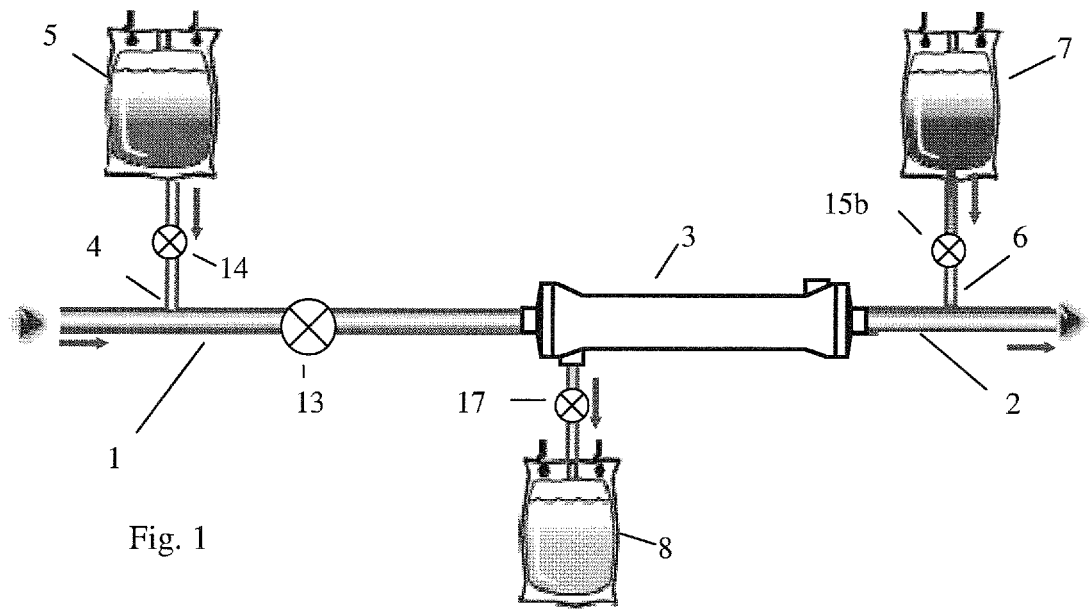
FIG. 1-8 shows different dialysis systems for regional citrate anticoagulation in an extracorporeal blood circuit.

The term "dialysis therapy" means all types of dialysis treatments both for chronic renal insufficiency and acute renal insufficiency.

The term "CRRT" means a continuous renal replacement therapy and this type of treatment mode is used in case of acute renal insufficiency or in case of chronic renal insufficiency when using a wearable artificial kidney system.

The term "filter" means a unit comprising semipermeable membranes. This unit may also be called a semipermeable membrane, a dialyzer, a dialysis filter or a dialysis membrane.

The term "anticoagulation fluid" means a fluid which is intended to provide for the anticoagulation effect within the extracorporeal blood circuit and which is intended to be infused within the extracorporeal blood circuit.

The term "anticoagulation fluid source" means the source of anticoagulation fluid. The source may be provided as fluid concentrate or in form of dry powder concentrate.

The term "treatment fluid" means a dialysis fluid for perfusion of a filter or an infusion fluid, i.e. a fluid for pre- or postinfusion. Thus, treatments fluid includes dialysis fluid, infusion fluid, replacement fluid, and substitution fluid.

The term "source of treatment fluid" means the source of treatment fluid, which may be provided as fluid concentrate or in form of dry powder concentrate.

The term "dialysis fluid" means a fluid for perfusion of a filter, on the dialysate side of such a filter, opposite the blood side.

The term "infusion fluid" means a fluid which is infused into the extracorporeal blood circuit either for predilution, i.e. infused into the extracorporeal blood flow before the blood enters the filter or for postdilution, i.e. infused into the extracorporeal blood flow after the blood has exited the filter and before the blood is returned to the patient. Infusion fluids are normally also named as replacement fluids, substitution fluids or hemofiltration fluids.

The term "total calcium concentration" means the total amount of calcium present in a fluid, thus representing the sum of calcium present as ionized, complex bound and protein bound calcium.

The term "citrate" means citric acid or any salt thereof. The salt may be formed with sodium, magnesium or potassium. The sodium citrate may be present as trisodium citrate, disodium hydrogencitrate, or monosodium dihydrogencitrate.

The term "basic citrate" means herein the tri-form of the citrate, thus the salt of $C_6H_5O_7^{3-}$. This salt may be formed with any of sodium, magnesium or potassium.

The term "acid citrate" means herein citric acid or the intermediate salt forms of the acid, thus the salt of hydrogen citrate and dihydrogen citrate, respectively. The acid citrate salts may be formed with any of sodium, magnesium or potassium.

The term "phosphate" means phosphoric acid or any salt thereof. The salt may be formed with sodium, magnesium, or potassium, The component may be added as phosphate ($PO_4^{3-}$), hydrogenphosphate ($HPO_4^{2-}$) or dihydrogen phosphate ($H_2PO_4^-$). Examples of salts are trisodium phosphate, disodium hydrogenphosphate, monosodium dihydrogenphosphate.1

DETAILED DESCRIPTION OF THE INVENTION

When patients receive continuous dialysis therapy, phosphate will be lost over the semipermeable membrane and administration of phosphate by intravenous routes must be carried out with great caution, as it is difficult to decide the correct amount of phosphate to be administered to the patient. If too much phosphate is administered hyperphosphatemia might develop, having serious consequences for the patient, for example hypocalcaemia, metastatic calcification and hypotension, and if too little phosphate is administered the hypophosphatemia is not corrected.

The regional anticoagulation systems of today with citrate as anticoagulant added in large volumes of anticoagulation fluids limits the amounts of available volume of the treatment fluids. In order to safeguard a proper phosphate balancing throughout the renal replacement treatment, the amount of phosphate needs to be balanced within as many of the used fluids as possible. By adding a balancing concentration of phosphate to at least one of the fluids, especially within the anticoagulation fluid, the phosphate level within the patient is better balanced throughout the treatment, and intravenous administration of phosphate may thereby be omitted, or at least reduced.

The anticoagulation fluid of the present invention comprises basic citrate in an amount of 10-40 mM; acid citrate in an amount of 0-5 mM; and phosphate in an amount of 0.1-4 mM. For example, the concentration of basic citrate may be selected to be 10, 12, 15, 18, 20, 22, 25, 30, 35 or 40 mM, which optionally can be combined with an amount of acid citrate, such as 0.5, 1, 1.5, 2, 2.5, 3, 3.5, 4, 4.5, or 5 mM acid citrate.

Phosphate may be included in an amount of 0.1 to 4 mM. For example, the anticoagulation fluid comprises phosphate in an amount of 0.1, 0.6, 0.7, 0.8, 0.9, 1.0, 1.1, 1.2, 1.3, 1.4, 1.5, 2, 2.5, 3, 3.5, or 4 mM.

The concentration of basic citrate and phosphate can be selected within the ranges, however it is advisable to combine a high concentration of basic citrate and a high level of phosphate, and in the same way, to include a lower concentration of phosphate in an anticoagulation fluid comprising lower amount of citrate. Examples of anticoagulation fluids comprises 10 mM basic citrate in combination with 1 mM phosphate, or 40 mM basic citrate in combination with 4 mM phosphate.

Further, an embodiment of the invention is an anticoagulation fluid comprising citrate and phosphate in concentrations as above, and in addition also comprises 0-150 mM sodium ($Na^+$). The anticoagulation fluid may comprise the sodium in a physiological amount.

The anticoagulation fluid of the invention has a pH between 6 and 8, preferably pH between 6.5 and 8. More preferably, the pH of the anticoagulation fluid may be between 7 and 8, such as 7.4, thus physiological pH. The pH can be adjusted by addition of a suitable acid, for example hydrochloric acid (HCl).

A further embodiment of the invention is an anticoagulation fluid comprising, in addition to the basic citrate and the phosphate, 0-1.5 mM magnesium, 0-4 mM calcium, 0-5.0 mM potassium, 0-11 mM glucose, and 0-150 mM sodium. An anticoagulation fluid as defined herein comprises 10-40 mM basic citrate; 0-5 acid citrate; 0.1-4 mM phosphate; 0-1.5 mM magnesium, 0-4 mM calcium, 0-5.0 mM potassium, 0-11 mM glucose, and 0-150 mM sodium. The anticoagulation fluid may be a physiological fluid.

The present invention concerns an anticoagulation fluid to be used as part of a multipart fluid system for dialysis therapy, wherein the multipart fluid system comprises an anticoagulation fluid and at least one treatment fluid from the group consisting of dialysis fluid and infusion fluids.

In one embodiment of the invention the anticoagulation fluid is used a part of a multipart fluid system for dialysis therapy. This multipart fluid system comprises the anticoagulation fluid and at least one treatment fluid from the group consisting of dialysis fluid and infusion fluids.

In one embodiment of the multipart fluid system the anticoagulation fluid comprises 10-40 mM citrate and 0.1-2.0 mM phosphate.

The treatment fluid to be combined with the anticoagulation fluid according to the invention may be a commercial available treatment fluid. An example is Hemosol B0. This is a treatment fluid containing Sodium 140 mM; Calcium 1.75 mM; Magnesium 0.5 mM; Potassium 0 mM; bicarbonate 32 mM; Lactate 3 mM; Glucose 0 mM; and chloride 109.5 mM.

Also phosphate containing treatment fluids may be combined with the anticoagulation fluid described herein.

Medical solutions suitable as treatment fluids are described in WO2006/041409A1. One of the herein described ready-for-use solutions comprises the following: Sodium 140 mM; Calcium 1.25 mM; Magnesium 0.6 mM; Potassium 4 mM; bicarbonate 30 mM; phosphate ($HPO_4^{2-}$) 1.2 mM; Glucose 5.0 mM; and chloride 115.9 mM.

Another treatment fluid, ready-for-use described contains the following: Sodium 140 mM; Calcium 1.5 mM; Magnesium 0.5 mM; Potassium 0 mM; bicarbonate 35 mM; phosphate ($HPO_4^{2-}$) 1.2 mM; Glucose 0 mM; and chloride 107.2 mM. A further another treatment fluid comprises Sodium 140 mM; Calcium 1.25 mM; Magnesium 0.6 mM; Potassium 4 mM; bicarbonate 0 mM; Lactate 35 mM; phosphate ($HPO_4^{2-}$) 1.2 mM; Glucose 5.0 mM; and chloride 145.9 mM. Another treatment fluid comprises Sodium 140 mM; Calcium 1.25 mM; Magnesium 0.6 mM; Potassium 4 mM; bicarbonate 6.6 mM; phosphate ($HPO_4^{2-}$) 1.2 mM; Glucose 5.0 mM; and chloride 114.9 mM.

Said anticoagulation fluid may, according one embodiment of the invention be used together with at least one infusion fluid comprising 0-5 mM total calcium, 0-8 mM citrate and 0.1-2.0 mM phosphate, with the provision that the infusion fluid comprises citrate when the total calcium concentration is 0 mM, or comprises calcium when the citrate concentration is 0 mM.

Said anticoagulation fluid may, according to another embodiment of the invention be used together with a dialysis fluid comprising 0-5 mM total calcium, 0-8 mM citrate and 0.1-2.0 mM phosphate, with the provision that the infusion fluid comprises citrate when the total calcium concentration is 0 mM, or comprises calcium when the citrate concentration is 0 mM.

An example of anticoagulation fluid according to the invention comprises 10-40 mM citrate and 0.1-2.0 mM phosphate, and is to be used together with one or more treatment fluids during a dialysis treatment.

The one or more treatment fluids may comprise 0-5 mM total calcium, 0-8 mM citrate, and 0.1-2.0 mM phosphate.

In one embodiment of the present invention said anticoagulation fluid comprises 0.5-2.0 mM phosphate, preferably 0.6-1.5 mM phosphate, and more preferably 0.8-1.2 mM phosphate. In another embodiment of the present invention said anticoagulation fluid or anticoagulation fluid comprises 10-40 mM citrate, preferably 15-40 mM citrate, and more preferably 20-30 mM citrate. In one embodiment said anticoagulation fluid may further comprise 1.5-4 mM total calcium, preferably 2-3 mM total calcium, more preferably 2.2-2.4 mM total calcium.

In yet another embodiment of the present invention said anticoagulation fluid further comprises 0-1.5 mM magnesium, 0-5.0 mM potassium, 0-11 mM glucose, 130-150 mM sodium. The anticoagulation fluid may also comprise chloride ions, for example in an amount of 0-140 mM chloride.

Further, the anticoagulation fluid may be used together with two infusion fluids, a first infusion fluid comprising 0-5 mM total calcium, 0-8 mM citrate and 0.1-2.0 mM phosphate, with the provision that the infusion fluid comprises citrate when the total calcium concentration is 0 mM, or comprises calcium when the citrate concentration is 0 mM; and a second infusion fluid comprising 0.1-2.0 mM phosphate. In one embodiment said second infusion fluid further comprises 0-5 mM total calcium, 0-8 mM citrate, with the provision that the second infusion fluid comprises citrate when the total calcium concentration is 0 mM, or comprises calcium when the citrate concentration is 0 mM.

Also, the anticoagulation fluid may according to even another embodiment of the invention be used together with at least one infusion fluid comprising 0-5 mM total calcium, 0-8 mM citrate and 0.1-2.0 mM phosphate, with the provision that the infusion fluid comprises citrate when the total calcium concentration is 0 mM, or comprises calcium when the citrate concentration is 0 mM; and a dialysis fluid comprising 0.1-2.0 mM phosphate. In one embodiment said dialysis fluid further comprises 0-5 mM total calcium, 0-8 mM citrate, with the provision that the dialysis fluid comprises citrate when the total calcium concentration is 0 mM, or comprises calcium when the citrate concentration is 0 mM.

The anticoagulation fluid may according to one embodiment of the invention be used together with at least one infusion fluid comprising 2-8 mM citrate.

The anticoagulation fluid may according to another embodiment of the invention be used together with a dialysis fluid comprising 2-8 mM citrate.

The anticoagulation fluid may according to another embodiment of the invention be used together with at least one infusion fluid comprising 2-8 mM citrate and 0.1-2.0 mM phosphate.

The anticoagulation fluid may according to a further embodiment of the invention be used together with a dialysis fluid comprising 2-8 mM citrate and 0.1-2.0 mM phosphate.

The anticoagulation fluid may according to one embodiment of the invention be used together with at least one infusion fluid comprising 2-8 mM citrate and 0.1-2.0 mM phosphate; and a dialysis fluid comprising 2-8 mM citrate and 0.1-2.0 mM phosphate.

The anticoagulation fluid may according to one embodiment of the invention be used together with at least one infusion fluid comprising 1-5 mM total calcium.

The anticoagulation fluid may according to another aspect of the invention be used together with a dialysis fluid comprising 1-5 mM total calcium.

The anticoagulation fluid may also be used together with at least one infusion fluid comprising 2-8 mM citrate and 1-5 mM total calcium.

The anticoagulation fluid may also be used together with a dialysis fluid comprising 2-8 mM citrate and 1-5 mM total calcium.

The anticoagulation fluid may also be used together with at least one infusion fluid comprising 2-8 mM citrate and 1-5 mM total calcium; and a dialysis fluid comprising 2-8 mM citrate and 1-5 mM total calcium.

The anticoagulation fluid may in one embodiment comprise 0.5-2.0 mM phosphate, preferably 0.6-1.5 mM phosphate, and more preferably 0.8-1.2 mM.

The anticoagulation fluid may in one embodiment comprise 10-40 mM citrate, preferably 15-40 mM citrate, more preferably 20-30 mM citrate. Said anticoagulation fluid may in one embodiment comprise 1.5-4 mM total calcium, preferably 2-3 mM total calcium, and most preferably 2.2-2.6 mM mM calcium.

The anticoagulation fluid may in one embodiment further comprise 0-1.5 mM magnesium, 0-5.0 mM potassium, 0-11 mM glucose, and 130-150 mM sodium. Also 0-140 mM chloride may be included in the anticoagulation fluid.

DETAILED DESCRIPTION OF THE DRAWINGS

FIGS. 1 to 8 illustrate different dialysis systems wherein the anticoagulation fluid may be used. In FIG. 1 is shown a first system for citrate anticoagulation in an extracorporeal blood circuit comprising an arterial blood line 1 configured to be connected to a vascular access (not shown) for withdrawing blood from a patient and a venous blood line 2 configured to be connected to the vascular access (not shown) for returning blood to the patient. This system comprises a filter 3 with a dialysate side and a blood side, which blood side is in fluid communication with the arterial blood line 1 and venous blood line 2; a pre-filter infusion line 4 connected to the arterial blood line 1 upstream the filter 3 for infusing an anticoagulation fluid 5 comprising 15-40 mM citrate into blood in the arterial blood line 1; and a post-filter infusion line 6 connected to the venous blood line 2 downstream the filter 3 for infusing an infusion fluid 7 comprising 1.5-8 mM citrate and 10 mM bicarbonate into blood in the venous blood line 2. An effluent bag 8 is provided in fluid communication with the dialysate side of the filter 3, to collect the plasma water (ultrafiltrate) withdrawn from the blood passing the filter 3.

Figure 2:
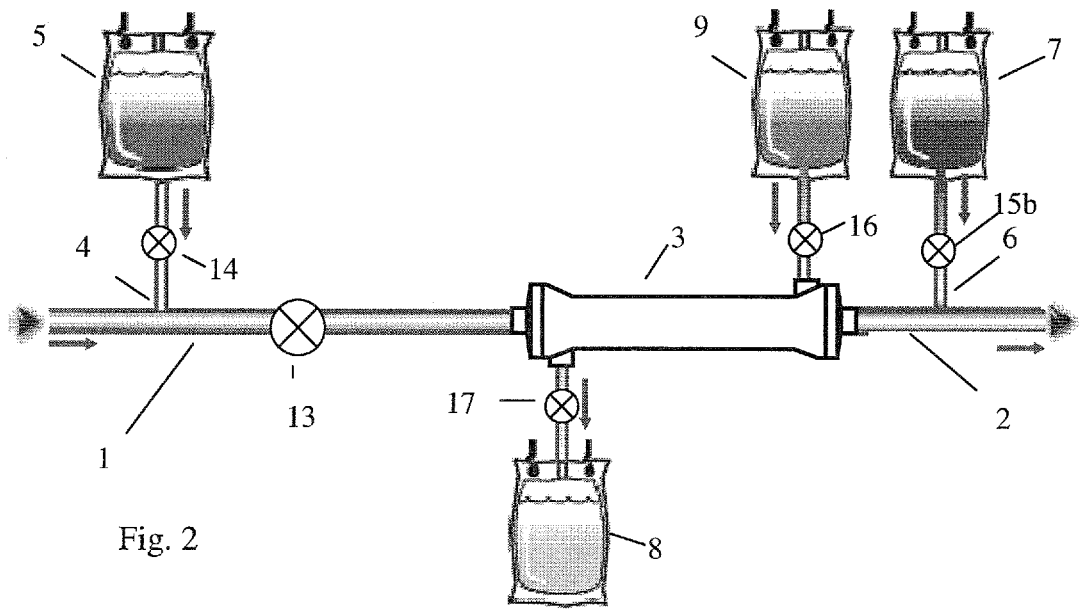

In FIG. 2 is shown another embodiment of the system in FIG. 1 with the addition that the dialysate side of the filter 3 is in fluid communication with a dialysis fluid source 9 comprising 1.5-8 mM citrate and 10 mM bicarbonate.

Figure 3:
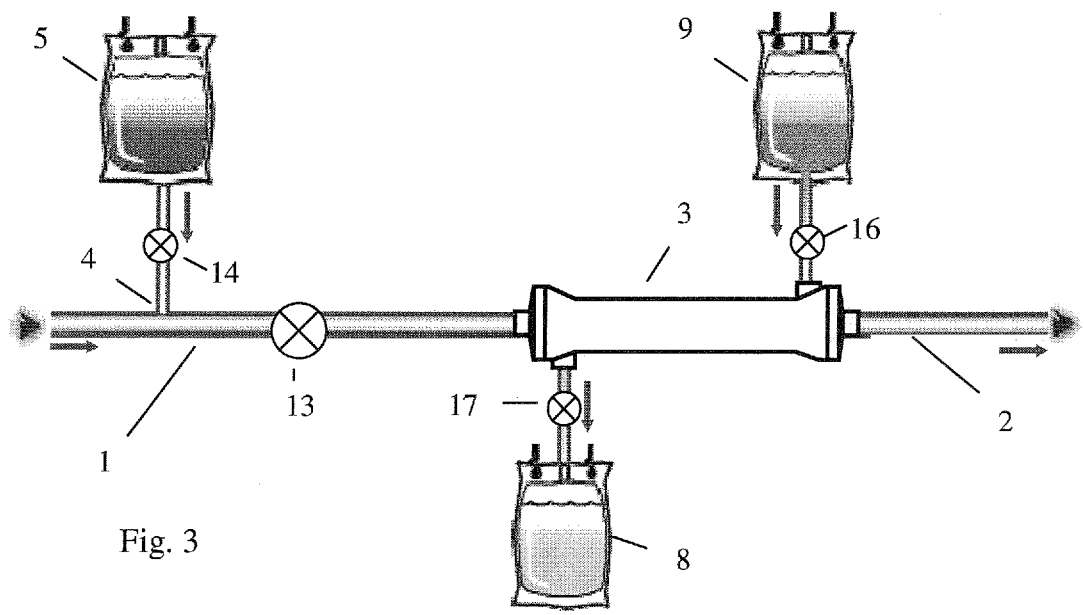

In FIG. 3 is shown a second system for citrate anticoagulation in an extracorporeal blood circuit. This system includes an arterial blood line 1 configured to be connected to a vascular access for withdrawing blood from a patient and a venous blood line 2 configured to be connected to the vascular access for returning blood to the patient. This system also comprises a filter 3 with a dialysate side and a blood side, which blood side is in fluid communication with the arterial and venous blood lines, and which dialysate side is in fluid communication with a dialysis fluid source 9 comprising 1.5-8 mM citrate and ≥10 mM bicarbonate and an effluent bag 8 for the spent dialysis fluid and the plasma water (ultrafiltrate) withdrawn from the blood passing the filter 3. The system further comprises a pre-filter infusion line 4 connected to the arterial blood line 1 upstream the filter 3 for infusing an anticoagulation fluid 5 comprising 15-40 mM citrate into the blood in the arterial blood line.

Figure 4:
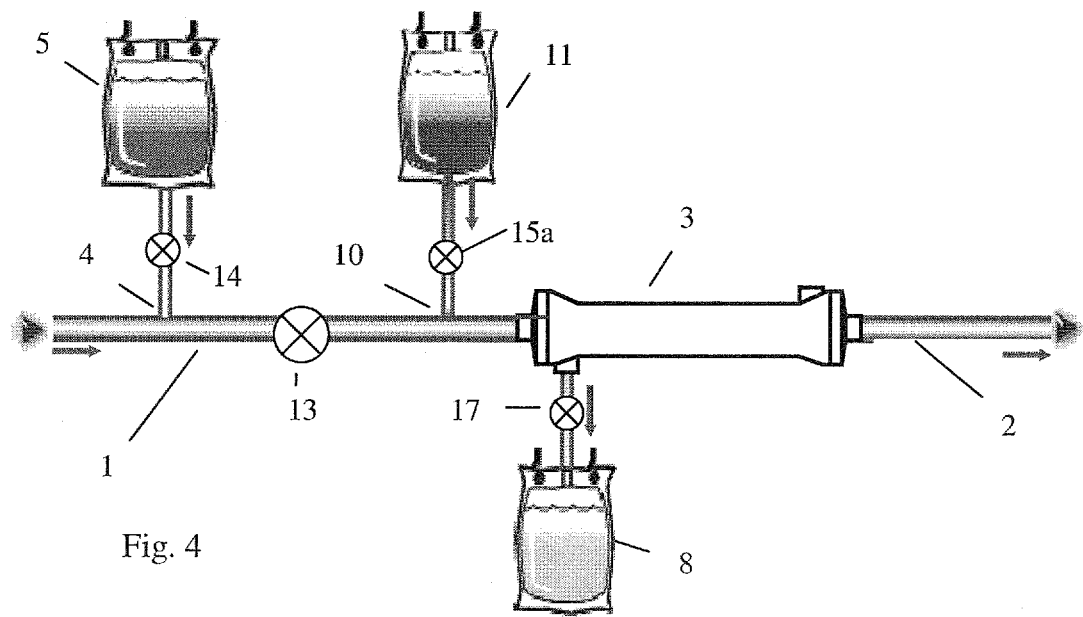

In FIG. 4 is shown a third embodiment of the system for citrate anticoagulation in an extracorporeal blood circuit according to the present invention. This system includes an arterial blood line 1 configured to be connected to a vascular access for withdrawing blood from a patient and a venous blood line 2 configured to be connected to the vascular access for returning blood to the patient. This system further comprises a filter 3 with a dialysate side and a blood side, which blood side is configured in fluid communication with the arterial and venous blood lines. A first pre-filter infusion line 4 is connected to the arterial blood line 1 upstream the filter 3 for infusing an anticoagulation fluid 5 comprising 15-40 mM citrate into blood in the arterial blood line 1. A second pre-filter infusion line 10 is connected to the arterial blood line 1 upstream the filter 3 for infusing an infusion fluid 11 1.5-8 mM citrate and ≥10 mM bicarbonate into blood in the arterial blood line 1. Also here an effluent bag 8 is provided in fluid communication with the dialysate side of the filter 3, for receiving the plasma water (ultrafiltrate) withdrawn from the blood passing the filter 3.

Figure 5:
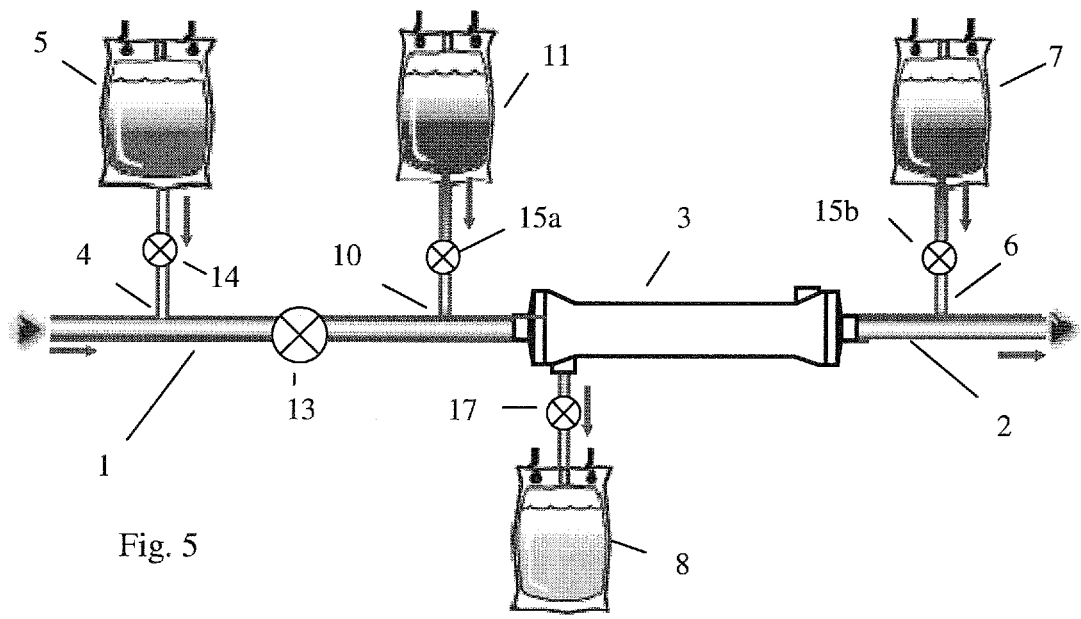

In FIG. 5 is another embodiment of the third system in FIG. 4 shown, which further comprises a post-filter infusion line 6 connected to the venous blood line 2 downstream the filter 3 for infusing an infusion fluid 7 comprising 1.5-8 mM citrate and ≥10 mM bicarbonate into blood in the venous blood line 2.

Figure 6:
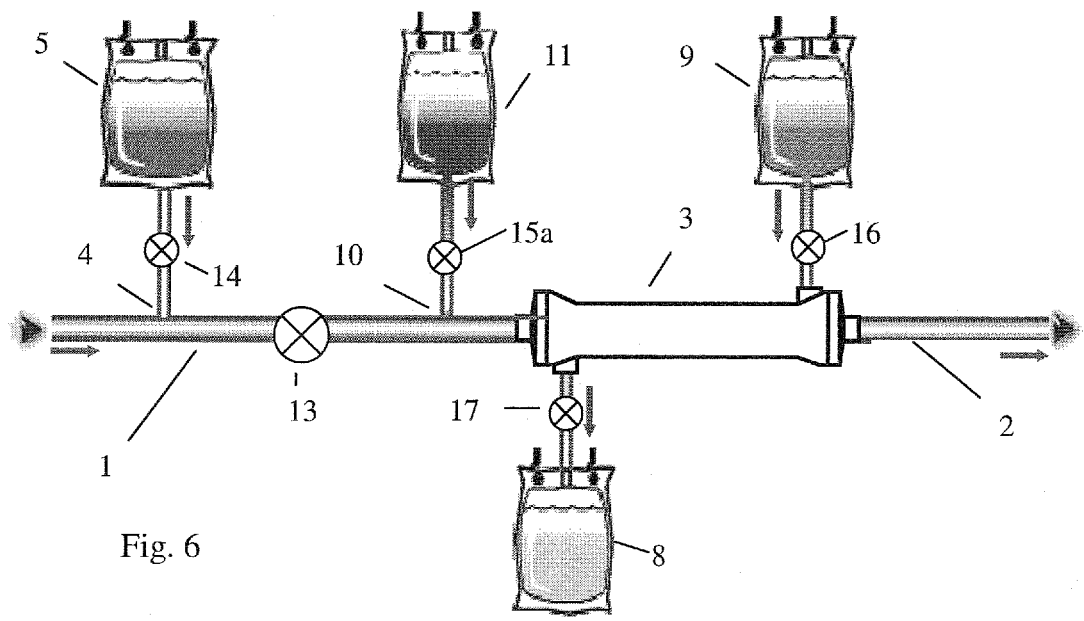

In FIG. 6 is yet another embodiment of the third system in FIG. 4 shown, wherein the dialysate side of the filter 3 is in fluid communication with a dialysis fluid source 9 comprising 1.5-8 mM citrate and ≥10 mM bicarbonate.

Figure 7:
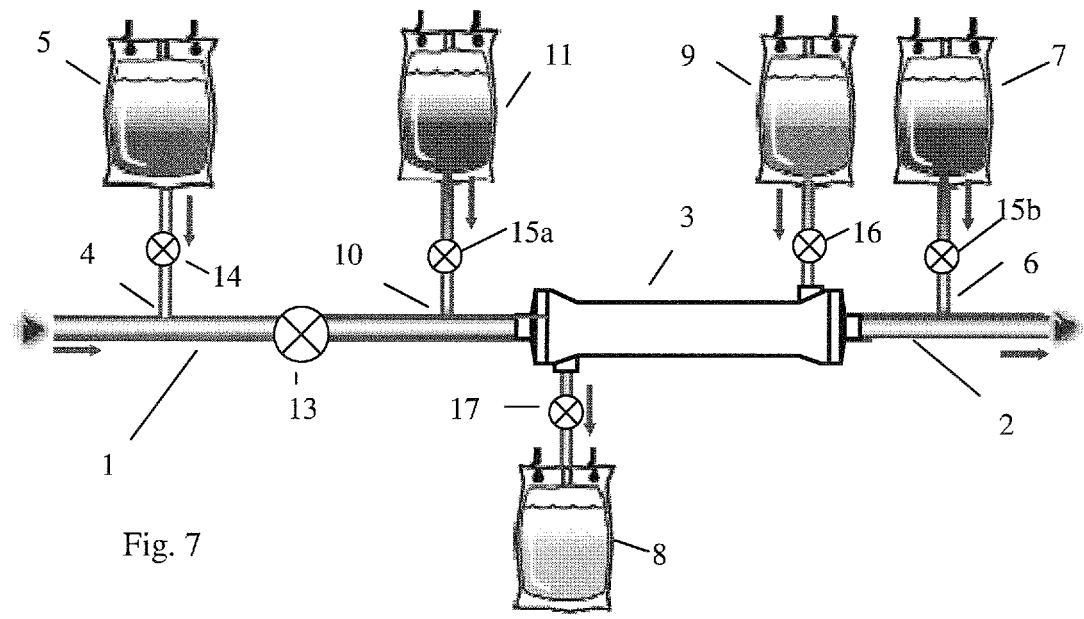

In FIG. 7 is another embodiment of the system in FIG. 6 shown. This system further comprises a post-filter infusion line 6 connected to the venous blood line 2 downstream the filter 3 for infusing an infusion fluid 7 comprising 1.5-8 mM citrate and ≥10 mM bicarbonate into the blood in the venous blood line 2.

Figure 8:
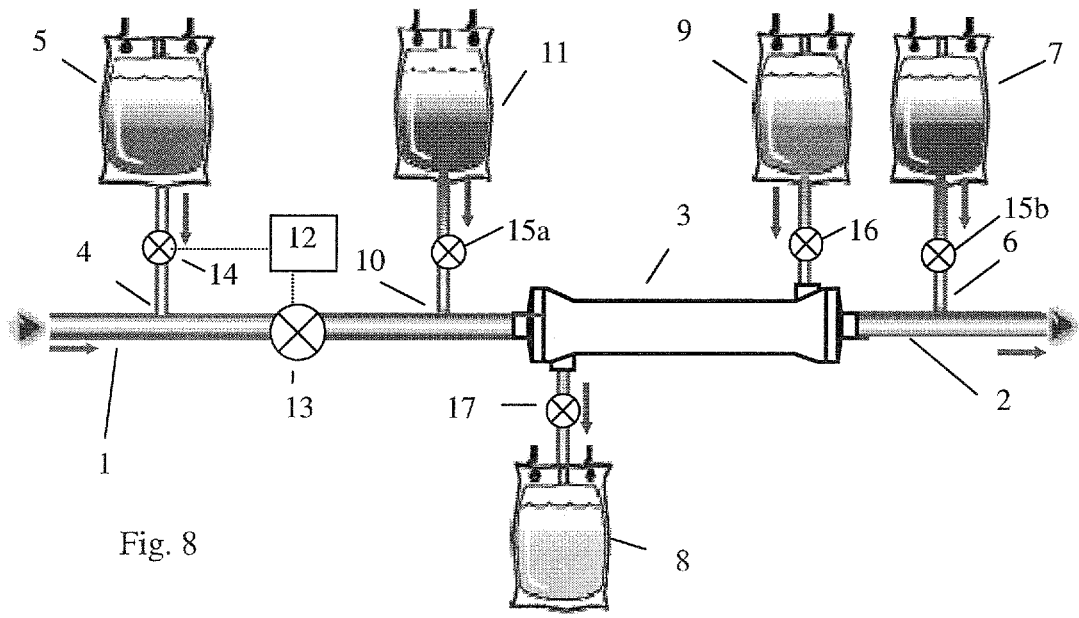

In FIG. 8 is another embodiment of the systems above shown, which further comprises a control unit 12 adapted to control the anticoagulation fluid flow rate in relation to the blood flow rate. Such a control unit may be provided in all the systems shown in the different embodiments of FIG. 1-FIG. 7. By having such a control unit 12, the system is monitoring and securing that the amount of citrate within the blood is enough to maintain anticoagulation within the extracorporeal blood circuit.

If 1-5 mM total calcium is present in at least one fluid from the group consisting of a dialysis fluid, an infusion fluid, and an anticoagulation fluid, the systems according to the present invention do not need to comprise any post-filter infusion line connected to the venous blood line 2 downstream the filter 3 for infusion of a fluid comprising >6 mM total calcium.

In the systems according to the invention, pumps are configured to pump blood (pump 13) through the extracorporeal blood circuit, anticoagulation fluid (pump 14) into the extracorporeal blood circuit, infusion fluid (pumps 15a and 15b) into the extracorporeal blood circuit, dialysis fluid (pump 16) into the dialysate side of the filter 3, and plasma liquid (ultrafiltrate) and optional spent dialysis fluid (pump 17) out from the dialysate side of the filter 3 and into the effluent bag 8.

An embodiment of the invention is an anticoagulation fluid comprising citrate and phosphate.

The anticoagulation fluid comprises 10-40 mM citrate, and between 0.1 and 4 mM phosphate.

EXAMPLES

By way of example, and not limitation, the following examples identify a variety of anticoagulation fluids comprising citrate and phosphate. Also multipart fluid systems including the anticoagulation fluids are shown.
The anticoagulation fluid comprises basic citrate in a concentration of 10-40 mM, acid citrate in a concentration of 0-5 mM, phosphate in a concentration of 0.6-4 mM, and sodium ($Na^+$) in a concentration of 0-150 mM. The anticoagulation fluid has a pH of between 6 and 8.

Example 1

The anticoagulation fluid according to this example comprises the following components:
Basic Citrate (mM): 10
Phosphate (mM): 0.8
Sodium ($Na^+$) (mM): 140

Example 2

The anticoagulation fluid according to this example comprises the following components:
Basic Citrate (mM): 12
Phosphate (mM): 0.8
Sodium ($Na^+$) (mM): 140

Example 3

The anticoagulation fluid according to this example comprises the following components:
Basic Citrate (mM): 15
Phosphate (mM): 0.8
Sodium ($Na^+$) (mM): 140

Example 4

The anticoagulation fluid according to this example comprises the following components:
Basic Citrate (mM): 18
Phosphate (mM): 0.8
Sodium ($Na^+$) (mM): 140

Example 5

The anticoagulation fluid according to this example comprises the following components:
Basic Citrate (mM): 20
Phosphate (mM): 0.8
Sodium ($Na^+$) (mM): 140

Example 6

The anticoagulation fluid according to this example comprises the following components:
Basic Citrate (mM): 22
Phosphate (mM): 0.8
Sodium ($Na^+$) (mM): 140

Example 7

The anticoagulation fluid according to this example comprises the following components:
Basic Citrate (mM): 25
Phosphate (mM): 0.8
Sodium ($Na^+$) (mM): 140

Example 8

The anticoagulation fluid according to this example comprises the following components:
Basic Citrate (mM): 30
Phosphate (mM): 0.8
Sodium ($Na^+$) (mM): 140

Example 9

The anticoagulation fluid according to this example comprises the following components:
Basic Citrate (mM): 10
Phosphate (mM): 0.6
Sodium ($Na^+$) (mM): 140

Example 10

The anticoagulation fluid according to this example comprises the following components:
Basic Citrate (mM): 12
Phosphate (mM): 0.6
Sodium ($Na^+$) (mM): 140

Example 11

The anticoagulation fluid according to this example comprises the following components:
Basic Citrate (mM): 15
Phosphate (mM): 0.6
Sodium ($Na^+$) (mM): 140

Example 12

The anticoagulation fluid according to this example comprises the following components:
Basic Citrate (mM): 18
Phosphate (mM): 0.6
Sodium ($Na^+$) (mM): 140

Example 13

The anticoagulation fluid according to this example comprises the following components:
Basic Citrate (mM): 20
Phosphate (mM): 0.6
Sodium ($Na^+$) (mM): 140

Example 14

The anticoagulation fluid according to this example comprises the following components:
Basic citrate (mM): 22
Phosphate (mM): 0.6
Sodium (Na$^+$) (mM): 140

Example 15

The anticoagulation fluid according to this example comprises the following components:
Basic citrate (mM): 25
Phosphate (mM): 0.6
Sodium (Na$^+$) (mM): 140

Example 16

The anticoagulation fluid according to this example comprises the following components:
Basic citrate (mM): 30
Phosphate (mM): 0.6
Sodium (Na$^+$) (mM): 140

Example 17

The anticoagulation fluid according to this example comprises the following components:
Basic Citrate (mM): 15
Phosphate (mM): 1.0
Sodium (Na$^+$) (mM): 140

Example 18

The anticoagulation fluid according to this example comprises the following components:
Basic citrate (mM): 18
Phosphate (mM): 1.0
Sodium (Na$^+$) (mM): 140

Example 19

The anticoagulation fluid according to this example comprises the following components:
Basic citrate (mM): 20
Phosphate (mM): 1.0
Sodium (Na$^+$) (mM): 140

Example 20

The anticoagulation fluid according to this example comprises the following components:
Basic citrate (mM): 22
Phosphate (mM): 1.0
Sodium (Na$^+$) (mM): 140

Example 21

The anticoagulation fluid according to this example comprises the following components:
Basic citrate (mM): 25
Phosphate (mM): 1.0
Sodium (Na$^+$) (mM): 140

Example 22

The anticoagulation fluid according to this example comprises the following components:
Basic citrate (mM): 30
Phosphate (mM): 1.0
Sodium (Na$^+$) (mM): 140

Example 23

The anticoagulation fluid according to this example comprises the following components:
Basic citrate (mM): 35
Phosphate (mM): 1.0
Sodium (Na$^+$) (mM): 140

Example 24

The anticoagulation fluid according to this example comprises the following components:
Basic citrate (mM): 15
Phosphate (mM): 1.2
Sodium (Na$^+$) (mM): 140

Example 25

The anticoagulation fluid according to this example comprises the following components:
Basic citrate (mM): 18
Phosphate (mM): 1.2
Sodium (Na$^+$) (mM): 140

Example 26

The anticoagulation fluid according to this example comprises the following components:
Basic Citrate (mM): 20
Phosphate (mM): 1.2
Sodium (Na$^+$) (mM): 140

Example 27

The anticoagulation fluid according to this example comprises the following components:
Basic citrate (mM): 40
Phosphate (mM): 1.2
Sodium (Na$^+$) (mM): 140

Example 28

The anticoagulation fluid according to this example comprises the following components:
Basic Citrate (mM): 18
Phosphate (mM): 1.5
Sodium (Na$^+$) (mM): 140

Example 29

The anticoagulation fluid according to this example comprises the following components:
Basic Citrate (mM): 20
Phosphate (mM): 1.5
Sodium (Na$^+$) (mM): 140

Example 30

The anticoagulation fluid according to this example comprises the following components:
Basic Citrate (mM): 30
Phosphate (mM): 1.5
Sodium (Na$^+$) (mM): 140

Example 31

The anticoagulation fluid according to this example comprises the following components:
Basic Citrate (mM): 40
Phosphate (mM): 1.5
Sodium (Na$^+$) (mM): 140

Example 32

The anticoagulation fluid according to this example comprises the following components:
Basic Citrate (mM): 30
Phosphate (mM): 2
Sodium (Na$^+$) (mM): 140

Example 33

The anticoagulation fluid according to this example comprises the following components:
Basic Citrate (mM): 40
Phosphate (mM): 2
Sodium (Na$^+$) (mM): 140

Example 34

The anticoagulation fluid according to this example comprises the following components:
Basic Citrate (mM): 30
Phosphate (mM): 3
Sodium (Na$^+$) (mM): 140

Example 35

The anticoagulation fluid according to this example comprises the following components:
Basic Citrate (mM): 40
Phosphate (mM): 3
Sodium (Na$^+$) (mM): 140

Example 36

The anticoagulation fluid according to this example comprises the following components:
Basic Citrate (mM): 30
Phosphate (mM): 4
Sodium (Na$^+$) (mM): 140

Example 37

The anticoagulation fluid according to this example comprises the following components:
Basic Citrate (mM): 40
Phosphate (mM): 4
Sodium (Na$^+$) (mM): 140

The anticoagulation fluid may also comprise further components, like electrolytes and glucose. The following examples identify such anticoagulation fluids.

| Component in anticoagulation fluid | Example 38 | Example 39 | Example 40 | Example 41 | Example 42 |
|---|---|---|---|---|---|
| Citrate, (mM) | 10 | 12 | 15 | 18 | 20 |
| Phosphate, (mM) | 0.8 | 0.8 | 0.8 | 0.8 | 0.8 |
| Calcium, (mM) | 2.4 | 2.2 | 2.2 | 2.2 | 2.2 |
| Magnesium, (mM) | 0.5 | 0.5 | 0.5 | 0.5 | 0.5 |
| Potassium, (mM) | 3 | 2 | 2 | 3 | 3 |
| Glucose, (mM) | 0 | 0 | 0 | 0 | 0 |
| Sodium, (mM) | 140 | 140 | 140 | 140 | 140 |

| Component in anticoagulation fluid | Example 43 | Example 44 | Example 45 | Example 46 | Example 47 |
|---|---|---|---|---|---|
| Citrate, (mM) | 22 | 25 | 25 | 25 | 30 |
| Phosphate, (mM) | 0.8 | 0.6 | 0.8 | 1.25 | 0.8 |
| Calcium, (mM) | 2.4 | 2.2 | 2.5 | 2.5 | 2.2 |
| Magnesium, (mM) | 0.5 | 0.7 | 0.5 | 0.5 | 0.8 |
| Potassium, (mM) | 3 | 4 | 3 | 3 | 3 |
| Glucose, (mM) | 0 | 0 | 0 | 0 | 0 |
| Sodium, (mM) | 140 | 140 | 140 | 140 | 140 |

| Component in anticoagulation fluid | Example 48 | Example 49 | Example 50 | Example 51 | Example 52 |
|---|---|---|---|---|---|
| Citrate, (mM) | 30 | 30 | 35 | 40 | 40 |
| Phosphate, (mM) | 1.0 | 1.25 | 0.8 | 1.0 | 3 |
| Calcium, (mM) | 2.4 | 2.5 | 2.2 | 2.3 | 2.5 |
| Magnesium, (mM) | 0.5 | 0.5 | 0.7 | 0.5 | 0.5 |
| Potassium, (mM) | 3 | 3 | 3 | 2 | 3 |
| Glucose, (mM) | 0 | 0 | 0 | 0 | 0 |
| Sodium, (mM) | 140 | 140 | 140 | 140 | 140 |

Evaluations

The new anticoagulation fluids according to the invention are intended to be used as a part in a multipart fluid system, and in a system for regional citrate anticoagulation. The fluids have been evaluated by use of simulation program developed in-house by Gambro. It computes equilibrium concentrations of species present in plasma and fluids used for dialysis by use of equilibrium constants (SCD base 2001[1]). Simulations according to system shown in FIG. 7. The species (electrolytes, albumin and formed complexes) taken into account are shown in Table 1.

TABLE 1

Normal plasma concentration of electrolytes and albumin together with the complexes taken into account formed with $Ca^{2+}$ and $Mg^{2+}$

| Specie | Normal plasma total conc (mM) (Kratz 1998[2]) | Complex formation with $Ca^{2+}$ and $Mg^{2+}$ |
|---|---|---|
| $Ca^{2+}$ | 2.1-2.6 (1.1-1.3 ionized) | |
| $Mg^{2+}$ | 0.7-1.0 | |
| $Na^+$ | 135-145 | |
| $Cl^-$ | 100-108 | |
| $HCO_3^-$, bicarbonate, bic | 22-26 | $CaHCO_3^+$, $MgHCO_3^+$ |
| Phosphate, $HPO_4^{2-}$; $H_2PO_4^-$ | 0.7-1.0 | $CaHPO_4$, $MgHPO_4$ |
| $C_6H_5O_7^{3-}$, citrate, cit | 0.1-0.3 (infants, Ames1950[3]) | Ca-cit$^-$, Ca-cit$_2^{4-}$, Mg-cit$^-$, Mg-cit$_2^{4-}$ |
| Albumin, alb | 0.5-0.6 | Alb-Ca$_n$, alb-Mg$_n$, n = 1-10 |

The transport of each species is governed by its mobility and the flow rates of plasma and dialysis fluid. Values for the mobility of different species are found in literature. The transport of ions is also affected by the demand for electroneutrality, which is expressed as the development of a membrane potential. In order to handle the effects of complex formations and albumin binding, the dialyzer is split up into a number of segments and the transport calculations are performed in an iterative manner. The transport across the dialyzer membrane in one segment leads to a new equilibrium for the complex formation and albumin binding, which forms the input to the next segment for the next iteration. About 30 iterations are needed to find the equilibrium concentrations along the entire dialyzer.

The requirements of the treatments are:
1. An adequate dialysis treatment
2. A sufficient anticoagulant effect, i.e. the ionized calcium through the blood side of the filter (dialyzer) must be 0.2-0.5 mM, preferably 0.3-0.4 (according to literature)
3. The plasma concentration of phosphate when returned to the patient has to be at normal level, i.e. about 0.7-1.0 mM.
4. The total plasma concentration of calcium when returned to the patient has to be at normal level, i.e. about 2.5 mM. Other electrolyte concentration levels must also be satisfactory.

In the following examples different multipart systems are presented. These have been evaluated in accordance with the above. The flow rates used at the evaluation is presented, they are denoted and explained as follows:

Qb—blood flow rate from patient;
Qpbp—pre blood pump flow rate;
Qpre—pre-filter treatment fluid rate;
Qpost—post filter treatment fluid flow rate; and
Qd—flow rate of dialysis fluid.

Example A

| Component | Anticoagulation fluid | Infusion fluid for postinfusion | Dialysis fluid |
|---|---|---|---|
| Citrate, (mM) | 30 | 0 | 4 |
| Phosphate, (mM) | 1.0 | 0.6 | 1.0 |
| Calcium, (mM) | 2.4 | 2.3 | 2.3 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 15 | 15 |

TABLE A

The result with multipart system according to Example A, with Qb 120 ml/min, Qpbp 16.0 ml/min, Qpre 0.0 ml/min, Qpost 4.8 ml/min, Qd 20.0 ml/min.

| | Concentration of plasma returning to patient (mmol/l) |
|---|---|
| Citrate, total | 4.29 |
| Phosphate, total | 1.06 |
| Calcium, total | 2.26 |
| Calcium, ionized | 0.43 |
| Bicarbonate (total $CO_2$) | 18.49 |
| Bicarbonate + citrate | 31.37 |
| pH | 7.60 |

Example B

| Component | Anticoagulation fluid | Infusion fluid for preinfusion | Dialysis fluid |
|---|---|---|---|
| Citrate, (mM) | 30 | 4 | 4 |
| Phosphate, (mM) | 1.0 | 0.6 | 1.0 |
| Calcium, (mM) | 2.4 | 0 | 2.3 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 15 | 15 |

TABLE B

The result of Example B, with Qb 120 ml/min, Qpbp 16.0 ml/min, Qpre 0.0 ml/min, Qpost 4.8 ml/min, Qdi 20.0 ml/min.

| | Concentration of plasma returning to patient (mmol/l) |
|---|---|
| Citrate, total | 4.54 |
| Phosphate, total | 1.06 |
| Calcium, total | 2.12 |
| Calcium, ionized | 0.38 |
| Bicarbonate (total $CO_2$) | 18.49 |
| Bicarbonate + citrate | 32.11 |
| pH | 7.62 |

Example C

| Component | Anticoagulation fluid | Infusion fluid for postinfusion | Dialysis fluid |
|---|---|---|---|
| Citrate, (mM) | 10 | 4 | 4 |
| Phosphate, (mM) | 0.8 | 0.8 | 0.8 |
| Calcium, (mM) | 2.4 | 2.2 | 2.2 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 35 | |

TABLE C

The result of Example C, with Qb 120 ml/min, Qpbp 48.0 ml/min, Qpre 0.0 ml/min, Qpost 27.2 ml/min, Qd 20.0 ml/min.

| | Concentration of plasma returning to patient (mmol/l) |
|---|---|
| Citrate, total | 3.70 |
| Phosphate, total | 1.03 |
| Calcium, total | 2.30 |
| Calcium, ionized | 0.52 |
| Bicarbonate (total $CO_2$) | 13.83 |
| Bicarbonate + citrate | 24.94 |
| pH | 7.59 |

Example D

| Component | Anticoagulation fluid | Infusion fluid for postinfusion | Dialysis fluid |
|---|---|---|---|
| Citrate, (mM) | 12 | 4 | 4 |
| Phosphate, (mM) | 0.8 | 0.8 | 0.8 |
| Calcium, (mM) | 2.2 | 2.2 | 2.2 |
| Magnesium, (mM) | 0.5 | 0.5 | 0.5 |
| Potassium, (mM) | 2 | 2 | 2 |
| Glucose, (mM) | 0 | 0 | 5.5 |
| Sodium, (mM) | 140 | 140 | 140 |
| Bicarbonate | 0 | 30 | 30 |

TABLE D

The result of Example D, with Qb 120 ml/min, Qpbp 40.0 ml/min, Qpre 0.0 ml/min, Qpost 19.2 ml/min, Qd 20.0 ml/min.

| | Concentration of plasma returning to patient (mmol/l) |
|---|---|
| Citrate, total | 3.96 |
| Phosphate, total | 1.02 |
| Calcium, total | 2.21 |
| Calcium, ionized | 0.46 |
| Bicarbonate (total $CO_2$) | 16.72 |
| Bicarbonate + citrate | 28.58 |
| pH | 7.62 |

Example E

| Component | Anticoagulation fluid | Infusion fluid for postinfusion | Dialysis fluid |
|---|---|---|---|
| Citrate, (mM) | 18 | 4 | 4 |
| Phosphate, (mM) | 0.8 | 0.8 | 0.8 |
| Calcium, (mM) | 2.2 | 2.2 | 2.2 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 30 | 30 |

TABLE E

The result of Example E Qb 120 ml/min, Qpbp 26.7 ml/min, Qpre 0.0 ml/min, Qpost 5.8 ml/min, Qd 20.0 ml/min.

| | Concentration of plasma returning to patient (mmol/l) |
|---|---|
| Citrate, total | 4.32 |
| Phosphate, total | 1.01 |
| Calcium, total | 2.21 |
| Calcium, ionized | 0.42 |
| Bicarbonate (total $CO_2$) | 20.56 |
| Bicarbonate + citrate | 33.53 |
| pH | 7.63 |

Example F

| Component | Anticoagulation fluid | Infusion fluid for postinfusion | Dialysis fluid |
|---|---|---|---|
| Citrate, (mM) | 25 | 4 | 4 |
| Phosphate, (mM) | 0.8 | 0.8 | 0.8 |
| Calcium, (mM) | 2.5 | 2.3 | 2.3 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 25 | 25 |

TABLE F

The result of Example F, with Qb 120 ml/min, Qpbp 26.7 ml/min, Qpre 0.0 ml/min, Qpost 5.8 ml/min, Qd 20.0 ml/min.

| | Concentration of plasma returning to patient (mmol/l) |
|---|---|
| Citrate, total | 4.49 |
| Phosphate, total | 1.00 |
| Calcium, total | 2.28 |
| Calcium, ionized | 0.42 |
| Bicarbonate (total $CO_2$) | 21.13 |
| Bicarbonate + citrate | 34.60 |
| pH | 7.62 |

Example G

| Component | Anticoagulation fluid | Infusion fluid for postinfusion | Dialysis fluid |
|---|---|---|---|
| Citrate, (mM) | 25 | 3 | 4 |
| Phosphate, (mM) | 1.25 | 0.6 | 1.25 |
| Calcium, (mM) | 2.5 | 2.3 | 2.3 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 15 | 15 |

TABLE G

The result of Example G, with Qb 120 ml/min, Qpbp 19.2 ml/min, Qpre 0.0 ml/min, Qpost 1.6 ml/min, Qd 20.0 ml/min

| | Concentration of plasma returning to patient (mmol/l) |
|---|---|
| Citrate, total | 4.46 |
| Phosphate, total | 1.17 |
| Calcium, total | 2.28 |
| Calcium, ionized | 0.42 |
| Bicarbonate (total $CO_2$) | 18.31 |
| Bicarbonate + citrate | 31.69 |
| pH | 7.62 |

Example H

| Component | Anticoagulation fluid | Infusion fluid for postinfusion | Dialysis fluid |
|---|---|---|---|
| Citrate, (mM) | 30 | 4 | 4 |
| Phosphate, (mM) | 1.25 | 0.6 | 1.25 |

-continued

| Component | Anticoagulation fluid | Infusion fluid for postinfusion | Dialysis fluid |
|---|---|---|---|
| Calcium, (mM) | 2.5 | 2.3 | 2.3 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 15 | 15 |

TABLE H

The result of Example H, with Qb 120 ml/min, Qpbp 16.0 ml/min, Qpre 0.0 ml/min, Qpost 4.8 ml/min, Qd 20.0 ml/min

| | Concentration of plasma returning to patient (mmol/l) |
|---|---|
| Citrate, total | 4.54 |
| Phosphate, total | 1.15 |
| Calcium, total | 2.28 |
| Calcium, ionized | 0.41 |
| Bicarbonate (total $CO_2$) | 18.49 |
| Bicarbonate + citrate | 32.12 |
| pH | 7.61 |

Example I

| Component | Anticoagulation fluid | Infusion fluid for postinfusion | Dialysis fluid |
|---|---|---|---|
| Citrate, (mM) | 40 | 4 | 4 |
| Phosphate, (mM) | 1.0 | 1.0 | 1.0 |
| Calcium, (mM) | 2.3 | 2.3 | 2.3 |
| Magnesium, (mM) | 0.5 | 0.5 | 0.5 |
| Potassium, (mM) | 2 | 2 | 2 |
| Glucose, (mM) | 0 | 0 | 5.5 |
| Sodium, (mM) | 140 | 140 | 140 |
| Bicarbonate | 0 | 15 | 15 |

TABLE I

The result of Example I, with Qb 120 ml/min, Qpbp 12.0 ml/min, Qpre 0.0 ml/min, Qpost 8.8 ml/min, Qd 20.0 ml/min.

| Result | Concentration of plasma returning to patient (mmol/l) |
|---|---|
| Citrate, total | 4.60 |
| Phosphate, total | 1.08 |
| Calcium, total | 2.25 |
| Calcium, ionized | 0.40 |
| Bicarbonate (total $CO_2$) | 18.67 |
| Bicarbonate + citrate | 32.48 |
| pH | 7.60 |

Example J

| Component | Anticoagulation fluid | Infusion fluid for postinfusion | Dialysis fluid |
|---|---|---|---|
| Citrate, (mM) | 35 | 5 | 5 |
| Phosphate, (mM) | 0.8 | 0.8 | 0.8 |
| Calcium, (mM) | 2.2 | 2.0 | 2.0 |
| Magnesium, (mM) | 0.7 | 0.7 | 0.7 |
| Potassium, (mM) | 3 | 3 | 3 |
| Glucose, (mM) | 0 | 5.5 | 5.5 |
| Sodium, (mM) | 140 | 140 | 140 |
| Bicarbonate | 0 | 15 | 15 |

TABLE J

The result of Example J, with Qb 120 ml/min, Qpbp 13.7 ml/min, Qpre 0.0 ml/min, Qpost 7.1 ml/min, Qd 20.0 ml/min.

| | Concentration of plasma returning to patient (mmol/l) |
|---|---|
| Citrate, total | 4.90 |
| Phosphate, total | 0.99 |
| Calcium, total | 2.14 |
| Calcium, ionized | 0.36 |
| Bicarbonate (total $CO_2$) | 18.61 |
| Bicarbonate + citrate | 33.62 |
| pH | 7.61 |

Example K

| Component | Anticoagulation fluid | Infusion fluid for postinfusion | Dialysis fluid |
|---|---|---|---|
| Citrate, (mM) | 25 | 4 | 4 |
| Phosphate, (mM) | 0.6 | 0.6 | 0.6 |
| Calcium, (mM) | 2.2 | 2.0 | 2.0 |
| Magnesium, (mM) | 0.7 | 0.7 | 0.7 |
| Potassium, (mM) | 4 | 4 | 4 |
| Glucose, (mM) | 0 | 5.5 | 5.5 |
| Sodium, (mM) | 140 | 140 | 140 |
| Bicarbonate | 0 | 15 | 15 |

TABLE K

The result of Example K, with Qb 120 ml/min, Qpbp 19.2 ml/min, Qpre 0.0 ml/min, Qpost 1.6 ml/min, Qd 20.0 ml/min

| | Concentration of plasma returning to patient (mmol/l) |
|---|---|
| Citrate, total | 4.48 |
| Phosphate, total | 0.92 |
| Calcium, total | 2.16 |
| Calcium, ionized | 0.40 |
| Bicarbonate (total $CO_2$) | 18.30 |
| Bicarbonate + citrate | 31.75 |
| pH | 7.61 |

Example L

| Component | Anticoagulation fluid | Infusion fluid for postinfusion | Dialysis fluid |
|---|---|---|---|
| Citrate, (mM) | 30 | 5 | 5 |
| Phosphate, (mM) | 0.8 | 0.8 | 0.8 |
| Calcium, (mM) | 2.2 | 2.0 | 2.0 |
| Magnesium, (mM) | 0.8 | 0.8 | 0.8 |
| Potassium, (mM) | 3 | 3 | 3 |
| Glucose, (mM) | 0 | 0 | 5.5 |

-continued

| Component | Anticoagulation fluid | Infusion fluid for postinfusion | Dialysis fluid |
|---|---|---|---|
| Sodium, (mM) | 140 | 140 | 140 |
| Bicarbonate | 0 | 15 | 15 |

TABLE L

The result of Example L, with Qb 120 ml/min, Qpbp 16.0 ml/min, Qpre 0.0 ml/min, Qpost 4.8 ml/min, Qd 20.0 ml/min.

| | Concentration of plasma returning to patient (mmol/l) |
|---|---|
| Citrate, total | 4.84 |
| Phosphate, total | 1.00 |
| Calcium, total | 2.15 |
| Calcium, ionized | 0.37 |
| Bicarbonate (total $CO_2$) | 18.50 |
| Bicarbonate + citrate | 33.00 |
| pH | 7.61 |

Example M

| Component | Anticoagulation fluid | Infusion fluid for postinfusion | Dialysis fluid |
|---|---|---|---|
| Citrate, (mM) | 30 | 4 | 4 |
| Phosphate, (mM) | 1.0 | 0.6 | 1.0 |
| Calcium, (mM) | 2.4 | 2.3 | 2.3 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 15 | 15 |

TABLE M

The result of Example M, with Qb 120 ml/min, Qpbp 16.0 ml/min, Qpre 0.0 ml/min, Qpost 4.8 ml/min, Qd 20.0 ml/min.

| | Concentration of plasma returning to patient (mmol/l) |
|---|---|
| Citrate, total | 4.54 |
| Phosphate, total | 1.06 |
| Calcium, total | 2.26 |
| Calcium, ionized | 0.41 |
| Bicarbonate (total $CO_2$) | 18.49 |
| Bicarbonate + citrate | 32.11 |
| pH | 7.61 |

Example N

| Component | Anticoagulation fluid | Infusion fluid for postinfusion | Dialysis fluid |
|---|---|---|---|
| Citrate, (mM) | 35 | 5 | 5 |
| Phosphate, (mM) | 0.8 | 0.8 | 0.8 |
| Calcium, (mM) | 2.2 | 2.0 | 2.0 |
| Magnesium, (mM) | 0.8 | 0.8 | 0.8 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 15 | 15 |

TABLE N

The result of Example N, with Qb 120 ml/min, Qpbp 13.7 ml/min, Qpre 0.0 ml/min, Qpost 7.1 ml/min, Qd 20.0 ml/min.

| Result | Concentration of plasma returning to patient (mmol/l) |
|---|---|
| Citrate, total | 4.90 |
| Phosphate, total | 0.99 |
| Calcium, total | 2.14 |
| Calcium, ionized | 0.36 |
| Bicarbonate (total $CO_2$) | 18.61 |
| Bicarbonate + citrate | 33.31 |
| pH | 7.61 |

Example O

| Component | Anticoagulation fluid | Infusion fluid for preinfusion | Dialysis fluid |
|---|---|---|---|
| Citrate, (mM) | 30 | 4 | 4 |
| Phosphate, (mM) | 1.0 | 0.6 | 1.0 |
| Calcium, (mM) | 2.4 | 0 | 0 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Bicarbonate | 0 | 15 | 15 |

TABLE O

The result of Example O, Qb 120 ml/min, Qpbp 16.0 ml/min, Qpre 4.8 ml/min, Qpost 0.0 ml/min, Qd 20.0 ml/min.

| | Concentration of plasma returning to patient (mmol/l) |
|---|---|
| Citrate, total | 4.60 |
| Phosphate, total | 1.07 |
| Calcium, total | 1.63 |
| Calcium, ionized | 0.26 |
| Bicarbonate (total $CO_2$) | 18.72 |
| Bicarbonate + citrate | 32.51 |
| pH | 7.66 |

With the balanced anticoagulation fluids together with the dialysis fluids and/or infusion fluids of the present invention the possibility to vary the flow rates of the different fluids within the multipart fluid system in a large interval without causing any acid-base imbalance within the patient is also provided.

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

REFERENCES

[1] SCDbase, Stability Constants Database IUPAC, Academic Software, 2001
[2] Kratz A et al.; New Engl J Med 339:1063-1067, 1998
[3] Ames R et al.; Pediatrics 6:361-370, 1950

The invention claimed is:

1. A single compartment bag comprising an anticoagulation fluid for regional citrate anticoagulation in an extracorporeal blood circuit, wherein the anticoagulation fluid in the single compartment bag comprises:
    18-40 mM basic citrate;
    0-5 mM acid citrate;
    0.1-3 mM phosphate; and
    1.5-4 mM calcium, the anticoagulation fluid having a pH between 7.4 and 8.

2. The single compartment bag according to claim 1, wherein the anticoagulation fluid comprises 0.5-2.0 mM phosphate.

3. The single compartment bag according to claim 1, wherein the anticoagulation fluid comprises 0-150 mM sodium.

4. The single compartment bag according to claim 1, wherein the anticoagulation fluid comprises 0-1.5 mM magnesium, 0-5.0 mM potassium, 0-11 mM glucose, and 0-150 mM sodium.

5. The single compartment bag according to claim 1, wherein the anticoagulation fluid comprises 18 mM basic citrate.

6. The single compartment bag according to claim 1, wherein the anticoagulation fluid comprises 20-40 mM basic citrate.

7. The single compartment bag according to claim 1, wherein the anticoagulation fluid comprises 0.8-2 mM phosphate.

8. The single compartment bag according to claim 1, wherein the anticoagulation fluid comprises 0 mM acid citrate.

* * * * *